United States Patent [19]
Kope

[11] Patent Number: 5,882,295
[45] Date of Patent: Mar. 16, 1999

[54] VIDEO CAMERA DRAPE

[75] Inventor: Stefan Kope, Carrolton, Tex.

[73] Assignee: Spectrum Medical Industries, Inc., Laguna Hills, Calif.

[21] Appl. No.: 58,939

[22] Filed: Apr. 13, 1998

[51] Int. Cl.[6] ................................................ A61B 1/04
[52] U.S. Cl. ................................................ 600/122
[58] Field of Search ................................ 600/121, 122, 600/123, 124, 125; 359/510

[56] References Cited

U.S. PATENT DOCUMENTS

| | | | |
|---|---|---|---|
| 4,522,196 | 6/1985 | Cunningham et al. | 600/122 X |
| 5,498,230 | 3/1996 | Adair | 600/122 X |

*Primary Examiner*—Beverly M. Flanagan
*Attorney, Agent, or Firm*—Edgar W. Averill

[57] ABSTRACT

An endoscopic video camera drape for completely segregating a video camera lens and camera assembly from an attached endoscopic lens assembly. The video camera is attached to a coupling. The coupling is shaped to hold a flared end of an endoscope. The drape has a conventional elongated flexible covering for covering the camera body and at least a portion of the cable of the camera. An optically transparent, flexible and tough polymeric film is attached in an airtight manner to the open end of the elongated flexible covering. The optically transparent bag is then placed over the coupling and is capable of receiving an endoscope and providing a transparent window between the video camera and endoscope without having to center a conventional rigid window.

Preferably the polymeric film bag is made from coextruded, biaxially oriented polypropylene film.

5 Claims, 2 Drawing Sheets

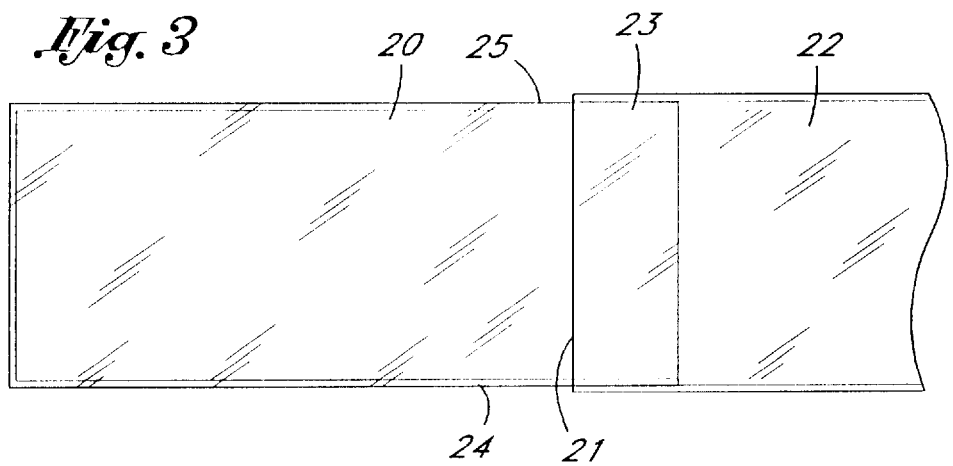
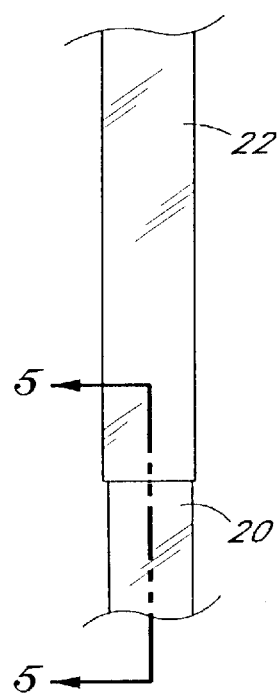
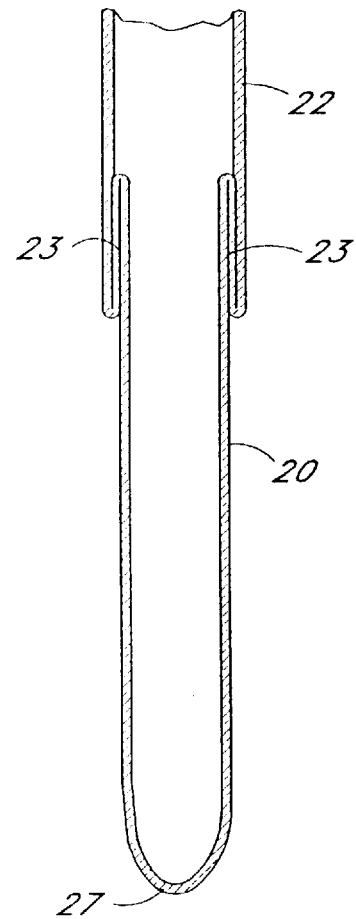

VIDEO CAMERA DRAPE

BACKGROUND OF THE INVENTION

The field of the invention is disposable sterilized covers and the invention relates more particularly to sterilizible video camera covers used with endoscopes.

In the past, video cameras used with endoscopes had to be completely sterilized. Various covers have been developed to eliminate this need. One such cover is shown in U.S. Pat. No. 4,522,196. This cover utilizes an elongated drape which has an aperture at its camera end which is centered utilizing a resilient elastomeric ring placed over the coupling. It is, of course, important that the ring be accurately centered and the opening provides the possibility of a lack of sterility. Two other approaches are shown in this same patent. One is shown in FIG. 6 where a pair of disks each have a central aperture. Portion 40 may be a separate end section or thin film exposed between the disks 42 and 46. The third embodiment shown in U.S. Pat. No. 4,522,196 is a rigid or semi-rigid optically clear molded portion 50 which is preformed in the shape of a cup which is placed over the intersection between the coupling and the endoscope. By using a rigid or semi-rigid optically clear material, the drape cannot be fully folded and the possibility of bending or wrinkling the optically clear material exists.

U.S. Pat. No. 4,914,521 utilizes a two-part coupling. One part goes over the camera and supports a flexible drape and the other part is the flexible drape adhered to the elongated coupling. This construction is, of course, limited to a particular camera and also cannot be folded into a flat configuration for storage and shipping.

BRIEF SUMMARY OF THE INVENTION

It is an object of the present invention to provide a transparent window between a video camera and an endoscopic assembly which is flexible and may be folded into a compact package with a conventional elongated flexible covering.

It is another object of the present invention to provide a window for an endoscopic video camera drape which does not need to be carefully centered between the camera and the endoscopic lens assembly.

The present invention is for an endoscopic video camera drape for completely segregating a video camera lens and cable assembly from an attached endoscopic lens assembly. The video camera has a receiving lens to which a coupling is affixed for attachment of a flared end of an endoscope. The video camera has a body and a cable which must be covered and the coupling has a closable receiving opening for receiving the flared end of an endoscope. An elongated flexible covering is made from conventional materials and covers the camera body and at least a portion of the camera cable. The elongated flexible covering has an open end at a camera end thereof and an open end at a cable end thereof. An optically transparent, flexible and tough polymeric film bag is attached in an airtight manner to the open end of the flexible covering at the camera end. The polymeric film bag in turn has an open end which is attached to the open end of the flexible covering and the polymeric film bag has closed walls and a closed bottom. When the drape is placed over the camera and coupling, the polymeric film bag may be placed with its bottom over the receiving opening of the coupling. When the flared end of an endoscope is inserted into the receiving end of a coupling the flexibility of the polymeric film bag causes it to form a flat, transparent window at an intersection of the flared end of the endoscope and the camera without the necessity of centering the rigid window over the intersection. Preferably, the film bag is fabricated from coextruded biaxially oriented polypropylene film. Preferably the film is between about 1.6 mils and 1.8 mils. Preferably the film bag is attached to the open end of the covering by double-sided adhesive tape. Preferably the side walls of the bag are closed by heat sealing thereby providing a bag which may be readily folded with the flexible covering to provide a thin assembly which may be easily stored and packaged.

BRIEF DESCRIPTION OF THE DRAWINGS

FIG. 3 is an enlarged view of the polymeric film bag attached to an open end of the elongated flexible covering.

FIG. 4 is a side view of the endoscopic video camera drape of the present invention.

FIG. 5 is a cross-sectional view taken along line 5—5 of FIG. 4.

DESCRIPTION OF THE PREFERRED EMBODIMENTS

Figure 1:
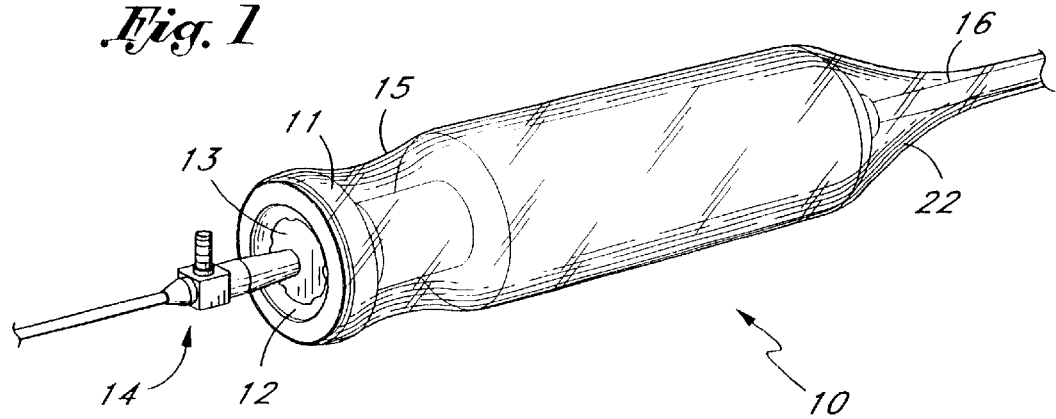
FIG. 1 is a perspective view of the flared end of an endoscope held in a coupling attached to a video camera which coupling and video camera are covered by an elongated flexible covering.

A video camera 10 is shown in a schematic manner in FIG. 1 and indicated by reference character 10. Video camera 10 has a coupling 11 held thereto. Coupling 11 has an opening 12 for receiving the flared end 13 of an endoscope 14. As is well known, it is possible to sterilize endoscope 14 but it is difficult and expensive to provide a video camera 10 which may be sterilized and thus, the video camera and coupling 11 are surrounded by an elongated flexible covering 15. Covering 15 not only covers video camera 10, but extends for a substantial length along cable 16 of camera 10. So far, the assembly is conventional. A problem has existed in the past to provide a window between the lens of video camera 10 indicated by reference character 17 in FIG. 2 and the window 18 of the endoscope 14. A commonly used drape has a small circular lens affixed to a flexible portion at the end of flexible cover 15. In practice, it has been found that the window is difficult to position in a manner that provides a positive coupling of the video camera assembly to the endoscope. In addition, a shadowing effect has been observed when the window is not well centered within the video camera assembly.

This problem has been solved by the use of an optically transparent flexible and tough polymeric film bag 20 which is sealed over the opening 21 of the elongated flexible covering 22. This bag is shown in side view in FIG. 3 where the bag is sealed over opening 21 by a double sided adhesive tape 23. Bag 20 is formed by being folded over and heat sealed along sides 24 and 25.

Figure 2:
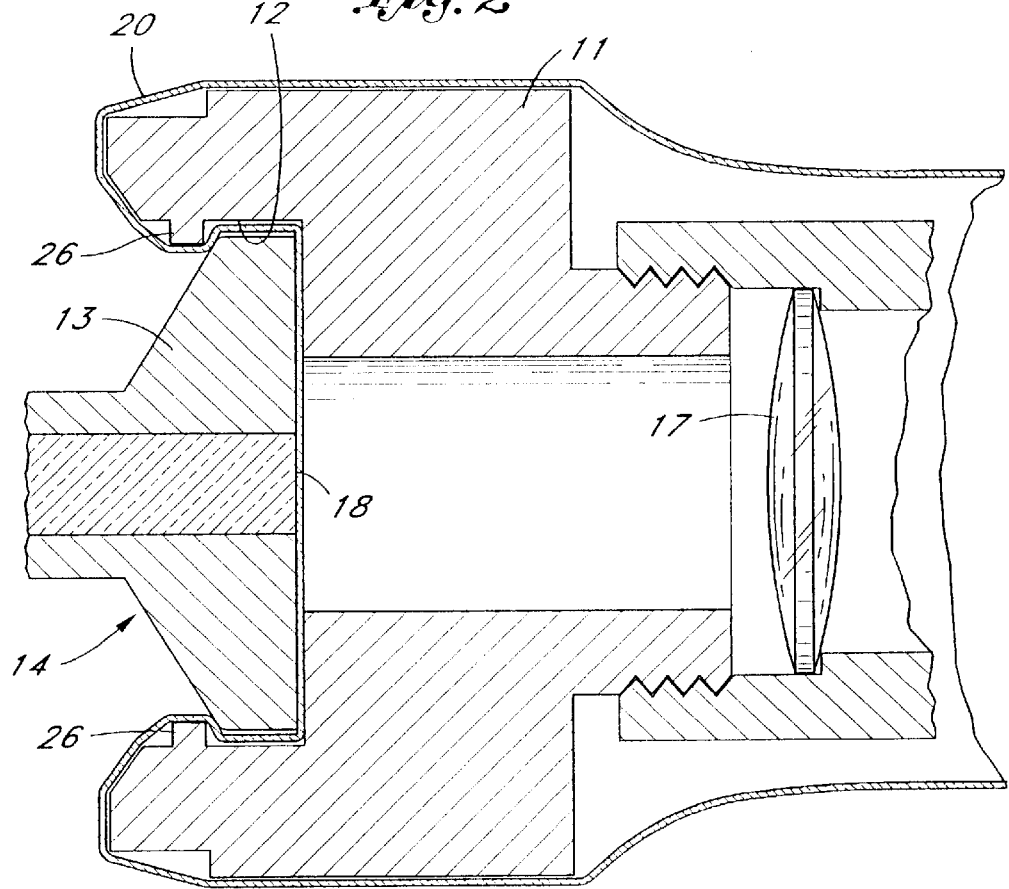
FIG. 2 is an enlarged cross-section view of the coupling and flared end of the endoscope of FIG. 1.

An enlarged cross-sectional view of the drape of the present invention is shown in FIG. 2 where coupling 11 is provided with an opening 12. Locking members 26 are moved to contact the flared end 13 of endoscope 14. These locking members are shown schematically in that there are several different types of locking members which form no part of the present invention. Since the locking members do contact the flared end 13, it is, however, important that the film bag 20 be strong enough to withstand this contact.

Film bag 20 is transparent and, thus, any part of it may be placed over window 18 of endoscope 14 and provide a clear view for lens 17 of video camera 10.

Although this may appear to be a simple solution, a myriad of polymeric films were tried before a film with sufficient clarity, toughness and flexibility was found. It has been found that coextruded, biaxially oriented, two-sided heat sealable polypropylene film having a thickness between about 1.6 mils and 1.8 mils provides an appropriate balance of properties for this stringent use. Not only is the film optically clear enough and strong enough, it also may be heat sealed as shown at reference characters 24 and 25 of FIG. 3 which enables the assembly shown in FIG. 4 to be very easily folded and stored. Furthermore, the bat 20 may be sterilized with ethylene oxide or gamma radiation. An enlarged view of the endoscopic camera drape of the present invention is shown in FIG. 5 which is taken along line 5—5 of FIG. 4. The bottom of the bag 20 is indicated by reference character 27 in FIG. 5. Since this portion is merely turned around as it is being heat sealed, it is not distorted in any way and will retain its excellent optical properties. Also, in FIG. 5, two portions of the double sided tape 23 are shown. Preferably the tape is about 1" wide to provide a complete seal between bag 20 and covering 22.

The result is an endoscopic video camera drape that completely segregates the video camera lens and cable assembly from the endoscopic lens assembly. This eliminates the need for sterilizing the video camera assembly. Because there is no need for centering a small lens, the placement of the drape of the present invention is especially easy.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. An endoscopic video camera drape for completely segregating a video camera lens and cable assembly from an attached endoscopic lens assembly, said video camera having a receiving lens end to which a coupling is affixed for attachment of a flared end of an endoscope and said video camera having a camera body and a cable, and said coupling having a receiving opening for receiving said flared end of an endoscope, said drape comprising:

an elongated flexible covering for covering the camera body and at least a portion of said cable, said elongated, flexible covering having an open end at a camera end and an open end at a cable end; and an optically transparent, flexible and tough polymeric film bag attached in an airtight manner to the open end at a camera end of said elongated flexible covering, said polymeric film bag having an open end which is attached to the open end at a camera end of said flexible covering and said polymeric film bag having closed walls and a closed bottom whereby said polymeric film bag may be placed with its bottom over said receiving opening for receiving said flared end of an endoscope and the flared end of an endoscope inserted into said receiving opening and the flexibility of the polymeric film bag causes it to form a flat transparent window at an intersection of said flared end and said coupling without the necessity of centering a rigid window over the intersection.

2. The endoscopic video camera drape of claim 1 wherein said optically transparent, flexible and tough polymeric film bag is fabricated from coextruded, biaxially oriented polypropylene film.

3. The endoscopic video camera drape of claim 2 wherein said polypropylene film is between about 1.6 and 1.8 mils.

4. The endoscopic video camera drape of claim 3 wherein said polypropylene film is attached in an air-tight manner to said open end at a camera end of said flexible covering by double sided adhesive tape.

5. The endoscopic video camera drape of claim 2 wherein the closed walls of said polymeric film bag are closed by heat sealing.

\* \* \* \* \*